US00PP16005P2

(12) United States Plant Patent
Brouwer

(10) Patent No.: US PP16,005 P2
(45) Date of Patent: Sep. 27, 2005

(54) ***SPATHIPHYLLUM* PLANT NAMED 'JETSON'**

(50) Latin Name: ***Spathiphyllum* sp.**
Varietal Denomination: Jetson

(76) Inventor: Wim A. J. Brouwer, Nieuwkoopseweg 47, 2631 PP Nootdorp (NL)

( * ) Notice: Subject to any disclaimer, the term of this patent is extended or adjusted under 35 U.S.C. 154(b) by 85 days.

(21) Appl. No.: 10/894,195

(22) Filed: Jul. 19, 2004

(51) Int. Cl.[7] ..... A01H 5/00
(52) U.S. Cl. ..... Plt./364
(58) Field of Search ..... Plt./364

*Primary Examiner*—Anne Marie Grunberg
(74) *Attorney, Agent, or Firm*—Mark P. Bourgeois

(57) ABSTRACT

A new cultivar of *Spathiphyllum* plant named 'Jetson' that is characterized by dark green leaves, a white spathe, a white spadix and a bushy habit with dense foliage.

1 Drawing Sheet

Botanical classification: *Spathiphyllum* sp.
Variety denomination: 'Jetson'.

BACKGROUND OF THE INVENTION

The present invention relates to a new and distinct cultivar of *Spathiphyllum* plant botanically known as *Spathiphyllum* and hereinafter referred to by the cultivar name 'Jetson'.

'Jetson' was discovered in the Spring of 2003 as a naturally occurring branch mutation of a plant of *Spathiphyllum* 'Jetty' (U.S. Plant Pat. No. 9,957). 'Jetson' was discovered in a cultivated area of Nootdorp, The Netherlands.

Asexual reproduction by tissue culture of the new cultivar 'Jetson' was first performed in November 2003 in Nootdorp, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Spathiphyllum* cultivar 'Jetson'.

1. *Spathiphyllum* 'Jetson' exhibits dark green leaves.
2. *Spathiphyllum* 'Jetson' exhibits a white spathe and spadix.
3. *Spathiphyllum* 'Jetson' exhibits a bushy habit with dense foliage.

The new cultivar 'Jetson' is distinguishable from the parent *Spathiphyllum* 'Jetty' by the following characteristics:

1. 'Jetson' flowers 3 to 4 weeks earlier.
2. 'Jetson' has darker leaves.
3. 'Jetson' has denser foliage.
4. 'Jetson' has a different color spathe. The spathe color of 'Jetson' is 155C. The spathe color of 'Jetty' is 155D.

BRIEF DESCRIPTION OF THE DRAWING

The accompanying photograph illustrates the distinguishing traits of *Spathiphyllum* 'Jetson'. The plant in the photograph shows an overall view of a 27 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Spathiphyllum* cultivar named 'Jetson'. Data was collected in Nootdorp, The Netherlands from 27 week old greenhouse grown plants in 21 cm containers. The time of year was Winter to Spring and the average temperature was 20° Centigrade during the day and night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'Jetson' has not been tested under all possible conditions and phenotypic differences may be observed with variations in environmental, climatic, and cultural conditions, however, without any variance in genotype.

Botanical classification: *Spathiphyllum* 'Jetson'.
Use: Ornamental.
Parentage: 'Jetson' is a branch sport of *Spathiphyllum* 'Jetty'.
Vigor: Moderate.
Growth rate: Moderate.
Growth habit: Freely clumping, outwardly arching, bushy and dense foliage.
Plant shape: Upright, somewhat outwardly spreading.
Suitable container size: 21 cm diameter container.
Height: Average 33 cm to top of leaf plane, 55 cm to top of inflorescences.
Width: Average 65 cm. in width.
Hardiness: USDA Zone 10.
Propagation: Tissue Culture.
Time to initiate roots (summer): Approximately 14 days to produce roots on an initial cutting.
Time to initiate roots (winter): Approximately 21 days to produce roots on an initial cutting.
Time to produce a rooted cutting or liner (summer and winter): Approximately 60 days.
Root system: Fine and fibrous.
Stem: No stems, Leaves grow directly from base, Average 5 clumps, clump color 143 A/B.

Foliage:

*Texture*.—Smooth, slightly leathery.
*Leaf arrangement*.—Alternate.
*Compound or single*.—Single.
*Leaf shape*.—*Ovate*.
*Leaf apex*.—*Apiculate*.
*Leaf base*.—*Attenuate*.
*Leaf length*.—*Average* 23.7 cm in length.
*Leaf width*.—12.3 cm in width.
*Pubescence*.—Absent.
*Leaf margin*.—Entire, slightly wavy.
*Vein pattern*.—Pinnate.
*Young leaf color* (*upper surface*).—Between 143 A/B and 144A.
*Young leaf color* (*lower surface*).—146B/C.
*Mature leaf color* (*upper surface*).—137B.
*Mature leaf color* (*lower surface*).—138B.
*Vein color* (*lower surface*).—144C.
*Vein color* (*upper surface*).—137B.
*Leaf attachment*.—Petiolate.
*Petiole dimensions*.—Average 17.1 cm in length including geniculum, 4 mm in diameter below geniculum to 9 mm. in diameter above clump.
*Petiole aspect*.—Round.
*Petiole color*.—137B.
*Geniculum dimensions*.—Average 2.6 cm in length and 4.7 mm in diameter.
*Geniculum aspect*.—Rounded.
*Geniculum color*.—138A.
*Petiole sheath dimensions*.—Average 14.1 cm in length and 5 mm in diameter.
*Petiole sheath color*.—137B/C.
*Durability of foliage to stress*.—High.

Inflorescence:

*Inflorescence arrangement*.—Spathes with spadices held above the foliage on erect peduncles arising from the petiole sheath.
*Flowering habit*.—Continuous.
*Quantity of spathes per plant*.—2 .
*Natural flowering season*.—Autumn to winter.
*Time to flower or response time*.—6 months.
*Fragrance*.—Strong, sweet.
*Self-cleaning or persistent*.—Persistent.
*Flower longevity*.—Lasts approximately 3 weeks on plant.
*Spathe aspect*.—Concave, cupped.
*Spathe dimensions*.—Average 15 cm in length, 10.9 cm in width and 6.2 cm in depth.
*Spathe texture*.—Glabrous, slightly leathery.
*Spathe shape*.—Broad elliptic.
*Spathe margin*.—Entire.
*Spathe apex*.—Apiculate, twisted.
*Spathe base*.—Cuneate.
*Spathe color when opening* (*front side*).—155C.
*Spathe color when opening* (*back side*).—155C.
*Spathe color when fully opened* (*front side*).—155C.
*Spathe color when fully opened* (*back side*).—155C with a vein 144A.
*Spathe color facing to*.—Not fading.
*Spadix shape*.—Columnar, arising from top of peduncle.
*Spadix dimensions*.—Average 9.3 cm in length and 1.7 mm in diameter.
*Spadix color when opening*.—158B.
*Spadix color when fully opened*.—158B.
*Quantity of flowers per spadix*.—Average 340.
*Spadix flower arrangement*.—Bisexual, rounded.
*Spadix flower dimensions*.—3.5 mm in diameter and 3 mm in depth.

Reproductive organs:

*Anther color*.—158D.
*Amount of pollen*.—Moderate to high.
*Pollen color*.—158C/D.
*Stigma color*.—58B.
*Ovary color*.—158B.

Peduncle:

*Peduncle dimensions*.—Average 41 cm in length and 5 mm. in diameter.
*Peduncle angle*.—0 to 10°.
*Peduncle color*.—137A/B.
*Peduncle strength*.—Strong.

Seed: Seed production has not been observed.

Disease and insect resistance: Plants of the new *Spathiphyllum* have not been observed for disease or insect resistance.

It is claimed:

1. A new and distinct variety of *Spathiphyllum* plant named 'Jetson' as described and illustrated.

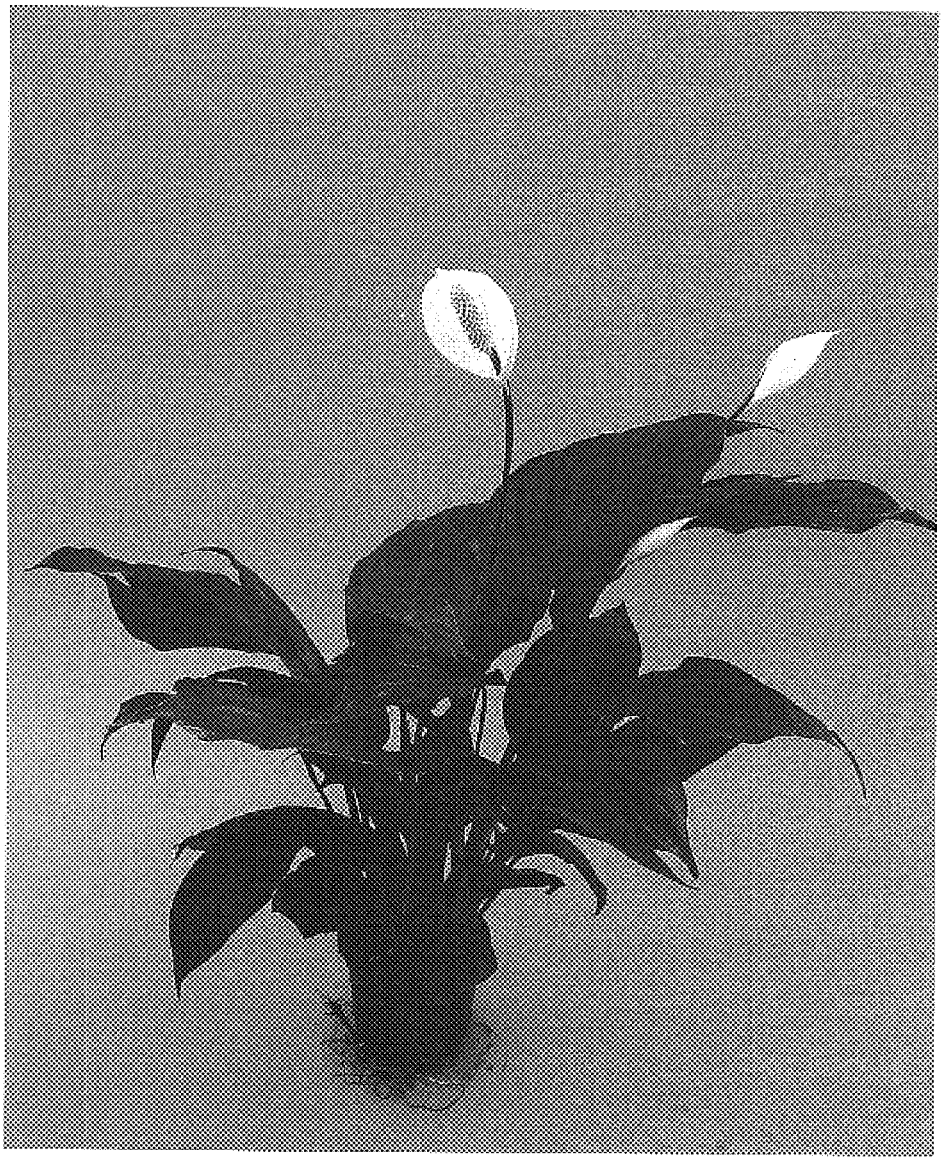

* * * * *